(12) United States Patent
Goyal et al.

(10) Patent No.: US 11,905,557 B2
(45) Date of Patent: Feb. 20, 2024

(54) PURIFICATION CHEMISTRIES AND FORMATS FOR SANGER DNA SEQUENCING REACTIONS ON A MICRO-FLUIDICS DEVICE

(71) Applicant: LIFE TECHNOLOGIES CORPORATION, Carlsbad, CA (US)

(72) Inventors: Swati Goyal, San Mateo, CA (US); Achim Karger, Foster City, CA (US); Peter Ma, Cupertino, CA (US); S. Jeffrey Rosner, Palo Alto, CA (US); Ian Walton, Redwood City, CA (US); Jonathan Wang, Mountain View, CA (US); Michael Wenz, Redwood City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 279 days.

(21) Appl. No.: 17/193,232

(22) Filed: Mar. 5, 2021

(65) Prior Publication Data
US 2021/0269871 A1 Sep. 2, 2021

Related U.S. Application Data

(63) Continuation of application No. 15/113,786, filed as application No. PCT/US2015/012777 on Jan. 23, 2015, now abandoned.
(Continued)

(51) Int. Cl.
*C12Q 1/6869* (2018.01)
*C12Q 1/6806* (2018.01)
*B01L 3/00* (2006.01)

(52) U.S. Cl.
CPC ...... *C12Q 1/6869* (2013.01); *B01L 3/502753* (2013.01); *C12Q 1/6806* (2013.01);
(Continued)

(58) Field of Classification Search
CPC ............ B01L 3/502753; C12Q 1/6869; C12Q 1/6806
See application file for complete search history.

(56) References Cited

U.S. PATENT DOCUMENTS 5,846,727 A   12/1998   Soper et al.
6,240,790 B1   6/2001   Swedberg et al.
(Continued)

FOREIGN PATENT DOCUMENTS

WO   200244414   6/2002

OTHER PUBLICATIONS

Blazej, R.G. et al., "Microfabricated bioprocessor for integrated nanoliter-scale Sanger DNA sequencing", PNAS, Vo. 103 (19), 2006, pp. 7240-7245.
(Continued)

*Primary Examiner* — Brian R Gordon
*Assistant Examiner* — Dwan A Gerido
(74) *Attorney, Agent, or Firm* — Jones Robb, PLLC

(57) ABSTRACT

According to various embodiments described herein, a microfluidics-chip based purification device and system for Sanger-sequencing reactions is provided. The device and system allow for the introduction into a sequencing system of a cartridge containing purification technologies specific to the sequencing contaminants or sequencing method where the simplified purification solution of a cartridge allows automation of the sample purification process, reduced consumption of purification reagents, and consistency in sampling by reducing the sampling errors and artifacts. These various embodiments therefore solve the need for a microfluidics-chip-based, Sanger-sequencing reaction purification system for CE devices. The microfluidic chips described can
(Continued)

be used as a PCR chip by reorganizing the on-chip reagents, reaction wells and work flow steps.

15 Claims, 3 Drawing Sheets

Specification includes a Sequence Listing.

Related U.S. Application Data

(60) Provisional application No. 61/931,549, filed on Jan. 24, 2014.

(52) U.S. Cl.
CPC ... *B01L 2200/0631* (2013.01); *B01L 2200/10* (2013.01); *B01L 2200/141* (2013.01); *B01L 2300/0887* (2013.01); *B01L 2300/12* (2013.01); *B01L 2300/16* (2013.01)

(56) References Cited

U.S. PATENT DOCUMENTS

| | | | |
|---|---|---|---|
| 6,818,760 | B1 | 11/2004 | Spicer et al. |
| 2002/0162804 | A1 | 11/2002 | Srinivasan et al. |
| 2003/0120061 | A1 | 6/2003 | Parthasarathy et al. |
| 2003/0120062 | A1 | 6/2003 | Parthasarathy et al. |
| 2004/0016702 | A1 | 1/2004 | Hennessy et al. |
| 2004/0209258 | A1* | 10/2004 | Parthasarathy .......... B01J 41/05 536/25.4 |
| 2005/0072674 | A1 | 4/2005 | Heins et al. |
| 2005/0106740 | A1 | 5/2005 | Boyes et al. |
| 2005/0133371 | A1* | 6/2005 | Timperman ..... G01N 27/44752 204/600 |
| 2005/0287572 | A1 | 12/2005 | Mathies et al. |
| 2008/0124721 | A1 | 5/2008 | Fuchs et al. |
| 2012/0292244 | A1* | 11/2012 | Harrold ................ B01J 20/3293 252/184 |
| 2012/0329142 | A1 | 12/2012 | Battrell et al. |
| 2015/0212056 | A1 | 7/2015 | Fairchild et al. |
| 2016/0084769 | A1 | 3/2016 | Chang et al. |

OTHER PUBLICATIONS

Elkin, et al., "Magnetic bead purification of labeled DNA fragments for high throughput capillary electrophoresis sequencing", Biotechniques, 32(6), 2002, pp. 1296, 1298-1300, 1302.

Invitrogen Dynal AS, "Dynabeads MyOne SILANE", http://www.bio-goods.com/Featured-Products/Dynal磁 ܾO;/2009617724685.pdf, Cat. No. 370,02D, 370.05D, Rev. No. 001, 2008, 2 pages.

PCT/US2015/012777 International Preliminary Report on Patentability and Written Opinion dated Aug. 4, 2016.

PCT/US2015/012777 International Search Report and Written Opinion dated Jun. 24, 2015.

* cited by examiner

```
                         SEQUENCE LISTING

<160> NUMBER OF SEQ ID NOS: 2

<210> SEQ ID NO 1
<211> LENGTH: 75
<212> TYPE: DNA
<213> ORGANISM: Homo sapiens

<400> SEQUENCE: 1
gtggctgcag cctggttatg attactgtta atgttgctac tactgctgac aatgctgctg      60
ctgcttctcc tcact                                                      75

<210> SEQ ID NO 2
<211> LENGTH: 111
<212> TYPE: DNA
<213> ORGANISM: Homo Sapiens

<400> SEQUENCE: 2
ccctggagga gaacaaaggc ttacttagtt ccctcatagg agaatgaaca gcaacaggga      60
aattattaaa tgcttaattc ggtaatgaca tacagtgtaa cagtgtgtca g              111
```

PURIFICATION CHEMISTRIES AND FORMATS FOR SANGER DNA SEQUENCING REACTIONS ON A MICRO-FLUIDICS DEVICE

CROSS-REFERENCE TO RELATED APPLICATIONS

This application is a continuation of U.S. application Ser. No. 15/113,786, filed Jul. 22, 2016, which is a national stage entry filed under 35 U.S.C. 371 of International Application No. PCT/US2015/012777 filed Jan. 23, 2015, which claims priority to U.S. Provisional Application Ser. No. 61/931,549 filed Jan. 24, 2014, and which aforementioned disclosures are herein incorporated by reference in their entireties.

BACKGROUND OF THE INVENTION

DNA sequencing is the process of determining the precise order of nucleotides within a DNA molecule. Two common sequencing methods are Sanger sequencing and "Next-Gen" sequencing, where Sanger sequencing is a method of DNA sequencing based on the selective incorporation of chain-terminating dideoxynucleotides (or ddNTPs) by DNA polymerase during in vitro DNA replication. While "Next-Gen" sequencing methods are typically used for large-scale, automated genome analyses, Sanger sequencing is primarily used for smaller-scale projects with the goal of obtaining especially long contiguous DNA sequence reads (>500 nucleotides). The use of labeled (either radioactively or fluorescently) amplification compounds (modified nucleotides or ddNTPs) for detection in automated sequencing machines typically results in contamination of subsequent sequences if the systems are not properly decontaminated and cleaned. Because avoidance of any overlap in amplification compound detection requires precise adjustment of all amplification products, the cleanup of, for example, fluorescence-based Sanger sequencing reactions is a crucial sample preparation step before subsequent sample analysis. In the context of other DNA purification methods, sequencing reaction purification or cleanup efforts generally focus on single-stranded DNA and generally requires expulsion to a high degree of the sequencing reaction contaminants, including buffering salts (de-salting), other ions, and unincorporated dye-ddNTP (dye-terminator) such that ionic strength is significantly reduced relative to the original reaction. For example, a target for residual salt level after purification could be less than or equal to 5 mM. Further, for dye terminators, a post-purification target could be greater than 1000-fold reduction from the original dye terminator concentration.

As a result, what is needed is a system to automate and simplify the generation of a clean sequencing sample that, except for the potential addition of certain compounds (such as formamide) and certain processes (such as heat-denaturation), yields a sequencing solution with low contaminant concentrations and is ready for electrokinetic injection and electrophoretic separation by capillary electrophoresis (CE).

A further need, for reasons discussed below, is the implementation of such a system for purification on a microfluidics chip, as known methods for purification have not been implemented on a microfluidics chip.

Purification of double-stranded DNA on microfluidics chips (for example, during the extraction and purification of biological samples such as whole blood or the clean up of PCR-products) have been largely described in the literature. However, only a limited amount of research has been devoted to systems allowing on-chip purification of Sanger sequencing single-stranded DNA reactions because sequencing is a very demanding application to integrate on a microchip, by requiring two rounds of thermocycling, with each requiring subsequent cleanup. Most published DNA assay chips (e.g., Rheonix Card®) are more modest in scope, implementing simpler workflows, or performing simple 1- or 2-step protocols like the gDNA preparation or one thermocycling PCR reaction alone.

One of the few publications demonstrating a microfluidics-based Sanger sequencing reaction cleanup (Mathies group of Blazej, Kumaresan and Mathies) describes an affinity capture/electro-elution chip functionality for the purpose of sequencing reaction clean-up. In particular, universal capture oligonucleotides covalently attached to the surface of a gel matrix 'capture gel' (created in one area of the chip) hybridize the sequencing products. Although this system allows for removal of charged impurities such as excess dye-terminator and salt by electrophoretic-elution, the sequencing reaction cleanup method requires the chip to be electrically connected and able to perform electrophoresis to function.

SUMMARY OF THE INVENTION

According to various embodiments described herein, a microfluidics-chip based purification device and system for Sanger-sequencing reactions is provided. The device and system allow for the introduction into a sequencing system of a cartridge containing purification technologies specific to the sequencing contaminants or sequencing method where the simplified purification solution of a cartridge allows automation of the sample purification process, reduced consumption of purification reagents, and consistency in sampling by reducing the sampling errors and artifacts. These various embodiments therefore solve the need for a microfluidics-chip-based, Sanger-sequencing reaction purification system for CE devices. Though the following focuses on Sanger-sequencing reaction purification systems for CE, the microfluidic chips described can be used as a PCR chip by reorganizing the on-chip reagents, reaction wells and work flow steps.

In an embodiment, a microfluidic sequencing reaction purification device is provided for reducing the number of sequencing contaminants in a single-stranded DNA sequencing sample. The microfluidics chip-based sequencing reaction purification device can comprising a surface, a solid-phase extraction substrate and silane bound to a structure. The structure can be selected from the group consisting of microstructures, the surface of the microfluidic device, a membrane, a high-surface area, convoluted material, and combinations thereof.

In another embodiment, a microfluidic sequencing reaction purification device is provided for reducing the number of sequencing contaminants in a single-stranded DNA sequencing sample. The microfluidic sequencing reaction purification device can comprise a surface and a reagent bound to a structure. The structure can be selected from the group consisting of microstructures, the surface of the microfluidic device, a membrane, a high-surface area, convoluted material, and combinations thereof.

In a further embodiment, a microfluidic sequencing reaction purification system is provided for reducing the number of sequencing contaminants in a single-stranded DNA sequencing sample and automating the purification process. The microfluidics chip-based sequencing reaction purification system can comprise a DNA sequencing system, a microfluidics device configured to operate within the DNA sequencing system. The microfluidics chip can comprise a surface and a reagent bound to a structure selected from the group consisting of a solid-phase extraction structure, microstructures, the surface of the microfluidics device, a membrane, a high-surface area, convoluted material, and combinations thereof.

DETAILED DESCRIPTION

Figure 1:
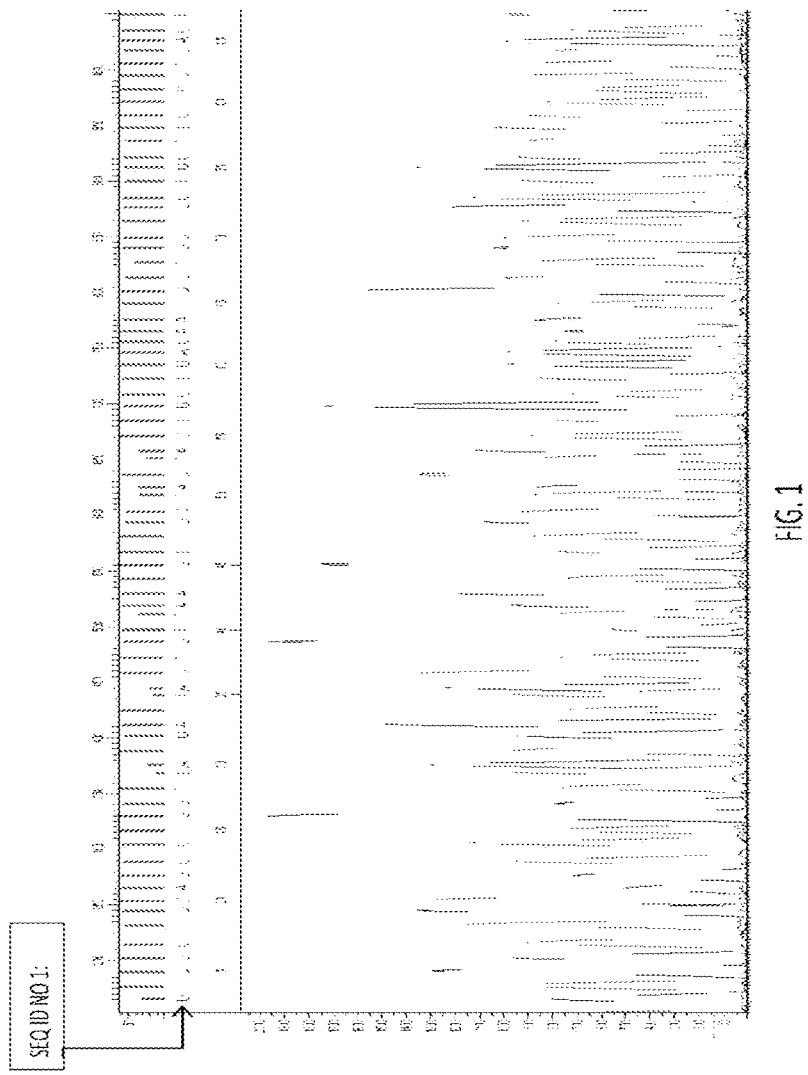
FIG. 1 illustrates sequencing data from sequence purified using ChargeSwitch® in 96 well plate.

The following description provides embodiments of the present invention. Such description is not intended to limit the scope of the present invention, but merely to provide a description of embodiments.

Several formats are possible for the implementation of purification media on a microfluidics device. Formats include, for example, micro-beads (for example polystyrene, latex beads or ion-exchange resin), modified surface on the microfluidics device, frits and membranes composed of DNA binding material and paramagnetic beads.

Combinations of non-limiting examples of purification methods and formats are summarized in the following table. Selection can be based on commercial availability, ease of implementation on a microfluidics device and least required R&D development effort.

| Chemistry/Format | (Non-magnetic) micro beads | Para-magnetic micro beads | Surface coating of the micro fluidics device | Membrane | Frit or wool material |
|---|---|---|---|---|---|
| Silane | | X | | | |
| ChargeSwitch ® | | X | X | | |
| BDX ® | X | | | | |
| PureLink ® | | | | X | |
| Hybridization based pull-out | | X | | | |
| Size Exclusion | X | | | | |

Each of these exemplary formats are discussed below in relation to exemplary purifications chemistries.

1. Purification by Solid Phase Extraction Utilizing Silane

Solid-phase extraction (SPE) is a separation process by which compounds (solutes) dissolved or suspended in a liquid mixture are separated from other compounds in the mixture according to their physical and chemical properties by using the affinity of the solutes for a solid through which the sample is passed to separate the mixture into distinct components. In one embodiment, the microfluidics-chip-based purification device is a solid phase extraction cartridge utilizing silane bound to microbeads, membranes, or microstructures within the device (e.g., plastic tubes or plates). In one embodiment, the microfluidics device and silane-coated microbeads is utilized in combination as a Sanger sequencing reaction purification system. In alternative embodiments, the silane-coated microbreads may comprise polystyrene, latex, agarose, an ion-exchange resin, an immobilized metal affinity chromatography (IMAC) resin, or any other substrate or resin capable of being coated by silane and utilized in a Sanger sequencing reaction purification system. In yet another embodiment of the purification system utilizing silane-coated microstructures (such as microbeads, tubes, plates, or any combination of these structures), the microstructures may be non-magnetic, magnetic, or paramagnetic. In yet another embodiment, the silane is bound to a structure including, but not limited to, a frit, a wool, a membrane or any other high-surface area, convoluted material, structure, or compound capable of being incorporated into a microfluidics device. The microfluidics device can be, for example, a microfluidic chip, card or cartridge.

In an embodiment, silane-coated microbeads (e.g., paramagnetic beads) bind single stranded DNA (ssDNA) and RNA. DNA can be bound in very low copy numbers. For example, as little as 10 copies of M13 single-stranded DNA could be captured and eluted from the paramagnetic beads. In a typical silane-coated bead purification protocol, 2 mg are used in a 400 μl bind reaction volume to capture approximately 5 μg of genomic double stranded DNA onto the surface of the paramagnetic micro beads. The conditions chosen for these experiments were such that the standard (tube)-scale amounts of beads (2 mg per assay) were used to extract the ssDNA in a 400 μl volume. Moreover, since the beads are paramagnetic, they can be easily immobilized in a microfluidic device (e.g., cartridge) format.

2. Purification by Reversible Ion-Exchange Binding of DNA

Reversible ion-exchange binding of DNA is a purification, separation, or decontamination process by which ions are exchanged between two electrolytes or between an electrolyte solution and a complex. The process typically involves solid polymeric or mineralic ion exchangers (e.g., ion exchange resins (such as functionalized porous or gel polymers), zeolites, and montmorillonite, clay, or soil humus). Ion exchangers can also include, for example, ionizable (or switchable) ion exchangers. In an embodiment of an ion-exchanger, the ion-exchanger comprises a surface ligand whose surface charge is a function of pH. The ion-exchanger surface ligand, for example, can be positively charged at low pH, and neutral at pH 8.5, to bind and elute plasmid.

In an alternative embodiment of the purification system, a microfluidics device comprising microstructures (such as microbeads, tubes, or plates) coated in at least one ion-exchanger is utilized as a Sanger sequencing reaction purification system. For example, the surface of the microfluidics device can be coated in at least one ion-exchanger. In another example, the microfluidics device can comprise a membrane coated with at least one ion-exchanger. In yet another example, the ion-exchanger can be bound to a structure including, but not limited to, a frit, a wool, a membrane or any other high-surface area, convoluted material, structure, or compound capable of being incorporated into a microfluidics device. In a further example, one or any combination of the microstructures, the device surface, a high-surface area structure, or a membrane can be coated in an ion-exchanger as described above. In another embodiment of the purification system utilizing ion-exchanger-coated microstructures (such as microbeads, tubes, plates, or any combination of these structures), the microstructures may be, for example, non-magnetic, magnetic, or paramagnetic. The microfluidics device can be, for example, a microfluidic chip, card or cartridge.

3. Purification by Size Exclusions and Ion-Exchange (SEIE)

Size exclusion and ion-exchange (SEIE) is a process in which molecules in solution are separated by their size (e.g., molecular weight) and charge. In an alternative embodiment of the purification system, a Sanger sequencing reaction purification system utilizes a microfluidics device and reagents specifically chosen to sequester reaction components based on the components charge and size. These reagents can be utilized by the microfluidics device to capture unincorporated dye exterminators, dNTPs, free salts, or salt ions generated during the sequencing reaction. The reagents can be bound to microstructures, where the microstructures may comprise microbeads, membranes, or structures within the chip (e.g., plastic tubes or plates). The reagents can be bound to microstructures (such as microbeads, tubes, plates, or any combination of these structures) that may be, for example, non-magnetic, magnetic, or paramagnetic. Alternatively, the reagents can be bound to the surface of the microfluidics device, or can also be bound to a structure including, but not limited to, a frit, a wool, a membrane or any other high-surface area, convoluted material, structure, or compound capable of being incorporated into a microfluidics device. Finally, the size-exclusion and ion-exchange reagents can be bound to one or any combination of microstructures, the surface of the microfluidics device, or a high-surface area, convoluted structure within the microfluidics device as described above. The microfluidics device can be, for example, a microfluidic chip, card or cartridge.

In contrast to other cleanup chemistry (bind-wash-elute style), size exclusion beads work by binding the known impurities. Sephadex® beads, for example are very cost-effective commercially available size exclusion beads that have the ability to extract terminators and salt while leaving the products of the sequencing reaction in solution. These beads advantageously have a relatively low cost. Moreover, they have been used routinely for sequencing reaction cleanup in conjunction with 96-well filter plates (for example, MultiScreen® 96w plates (Durapore® or Ultracell®—10 filter) from Millipore).

4. Purification by Membrane

Purification by membrane is a mechanical separation process in which undesirable sequencing solution reaction compounds are removed from the system using binding buffers and a porous physical structure (such as a membrane) through which the bound reaction compounds cannot pass. In one embodiment, the system uses at least one binding buffer and at least one porous structure configured to remove reaction compounds such as short primers, dNTPs, enzymes, short-failed PCR/CE products, salts from PCR/CE products, or any combination thereof. In an alternative embodiment of the purification system, a Sanger sequencing reaction purification system utilizes a microfluidics device comprising at least one binding buffer and at least one membrane. The membrane may be any structure including, but not limited to, a frit, a wool, a membrane, or any porous, high-surface structure through which a solution may pass. The microfluidics device can be, for example, a microfluidic chip, card or cartridge. An example of purification by membrane is PureLink®, manufactured by Life Technologies.

5. Purification by Hybridization-Based Pull-Out

Hybridization-based pull-out is based on hybridization-binding of the sequencing reaction products to a complementary oligonucleotide that is attached or bound to a microstructure or the surface of the microfluidics device. In an embodiment of the purification system, a Sanger sequencing reaction purification system utilizes a microfluidics device comprising at least one hybridization-based pull-out oligonucleotide selected to be complementary to a sequencing reaction product. In an alternative embodiment, the hybridization-based pull-out oligonucleotide is bound to a microstructure or the surface of the microfluidics device. In another embodiment of the purification system utilizing hybridization-based pull-out oligonucleotides bound to microstructures (such as microbeads, tubes, plates, or any combination of these structures), the microstructures may be, for example, non-magnetic, magnetic, or paramagnetic. The hybridization-based pull-out oligonucleotide can be bound to a structure including, but not limited to, a frit, a wool, a membrane or any other high-surface area, convoluted material, structure, or compound capable of being incorporated into a microfluidics device. The hybridization-based pull-out oligonucleotide can also be bound to one or any combination of microstructures, the surface of the microfluidics device, or a high-surface-area, convoluted structure as described above. The microfluidics device can be, for example, a microfluidic chip, card or cartridge.

Hybridization beads, for example, with capturing oligonucleotide attached to its surface, can be made by numerous manufacturing processes including, for example, the process used to manufacture Anti-miRNA Bead Capture (ABC) beads. The ABC kit is a commercialized product for capturing specific miRNA from a biological sample (e.g., blood) directly. It can use a complementary oligonucleotide on a magnetic bead to hybridized and capture specific miRNA. The bead-oligo linkage is covalent and permanent using the well-known carboxy (on bead), NH-ester (on oligo) standard chemistry.

6. Purification Combining Multiple Purification Methods

In another embodiment, the microfluidics device comprises multiple technologies, including, but not limited to, solid-phase extraction technology utilizing silane, reversible ion exchange binding of DNA, size exclusion and ion-exchange technology, membrane technology, and hybridization-based pull-out technology.

EXAMPLES

ChargeSwitch® (product of Life Technologies) Purification example of reversible IE binding of DNA:

Polymer Preparation:
  Bis-Tris is reacted with Polyacrylic Acid in the presence of EDC to yield a polymer containing bound Bis-Tris.
  Polymer bound Bis-Tris can be protonated by acid (H+) in acidic conditions producing a positive charged surface. The positively charged polymer selectively binds to DNA.
  At higher pH (>8), the polymer should still be water soluble and have no charge; effectively enabling elution of bound DNA Protocol to Coat Polymer on Solid Surface:
  1. Polymer can be diluted in 1% PB buffer.
  2. 100 µl of 10-100% polymer is added to the solid surface to be coated.
  3. Wait 15 min and discard polymer from the surface
  4. Add 100 µl of 1% PB buffer, wait 2 min and remove the buffer
  5. Step 4 is repeated again
  6. Air dry solid surface for at least 2 hours Protocol to purify sequencing reactions
  a. With polymer coated on solid surface.
    1. Add 10 µl of sample to the coated surface.
    2. Bind the sample by adding and equivalent volume (10 µl) of DCB to it.

3. Incubate for 15 min, remove the liquid completely.
4. Wash the sample by adding 150 µl of DCBW to the plate location
5. Incubate for 1 min, remove the liquid completely
6. A final wash of sample is done by flowing 150-200 µl of nuclease-free-water over the surface
   (If possible, minimize the time from adding the water to removing it in step 11 as much as possible to prevent possible elution of the bound sample.)
7. Elute the sample by adding 10 µl of HDF or Tris HCl (pH 8.5)
8. Incubate for 5 min and then collect the supernatant b. With polymer coated on magnetic beads.
   1. To 10 µl of sample, add 10 µl DCB-12 buffer and 2 µl of beads (stable at RT)
   2. Mix and incubate at RT for 7 ruin
   3. Magnetize beads and discard supernatant
   4. Demagnetize and add 150 µl of DCBW6 wash buffer and mix
   5. Magnetize beads and discard supernatant
   6. Repeat step 4 & 5
   7. Demagnetize and add 10 µl of elution buffer
   8. Mix and incubate for 5 min
   9. Magnetize beads and collect supernatant to sample outlet FIG. 1 illustrates sequencing data from sequence purified using ChargeSwitch® in 96 well plate.

DynaBeads® Purification example of SPE:

Bead Preparation:

Dynabeads® MyOne™ SILANE (product of Life Technologies) are supplied at a concentration of 40 mg/ml. Prior to use, the beads should be transferred to the appropriate binding solution as follows:
1. Re-suspend the Dynabeads® MyOne™ SILANE completely (e.g. vortex) to a homogenous suspension prior to use. Leave on a roller until use.
2. Transfer 400 µl of re-suspended Dynabeads® MyOne™ SILANE to a fresh tube. Place the tube on the magnet until the supernatant is clear, then remove and discard the supernatant.
3. Re-suspend in 13.33 µl of 40% TEG (tetraethlyene glycol)
4. Add 240 µl 100% ethanol and mix thoroughly.
5. The final bead-solution used in the isolation protocol described below should contain Dynabeads® MyOne™ SILANE at 1.5 mg/ml in 2% TEG/90% ethanol.

Protocol for Sequence Clean-Up
6. Add 20 µl (30 µg) Dynabeads® MyOne™ SILANE (supplied in TEG and ethanol, see above) to 10 µl sequencing reaction mix.
7. Mix and incubate for 10 minutes at room temperature.
8. Magnetize the beads and remove the supernatant completely.
9. Demagnetize and re-suspend the Dynabeads® MyOne™ SILANE in 30 µl 55% ethanol.
10. Magnetize the beads and remove the supernatant completely.
11. While still on the magnet, let the Dynabeads® MyOne™ SILANE pellet air-dry for 5 minutes at room temperature.
12. Demagnetize and re-suspend the Dynabeads® MyOne™ SILANE in 10 µl water.
13. Incubate for 3 minutes at room temperature.
14. Magnetize beads again and transfer the supernatant containing the sequencing products for sequencing readout.

Figure 2:
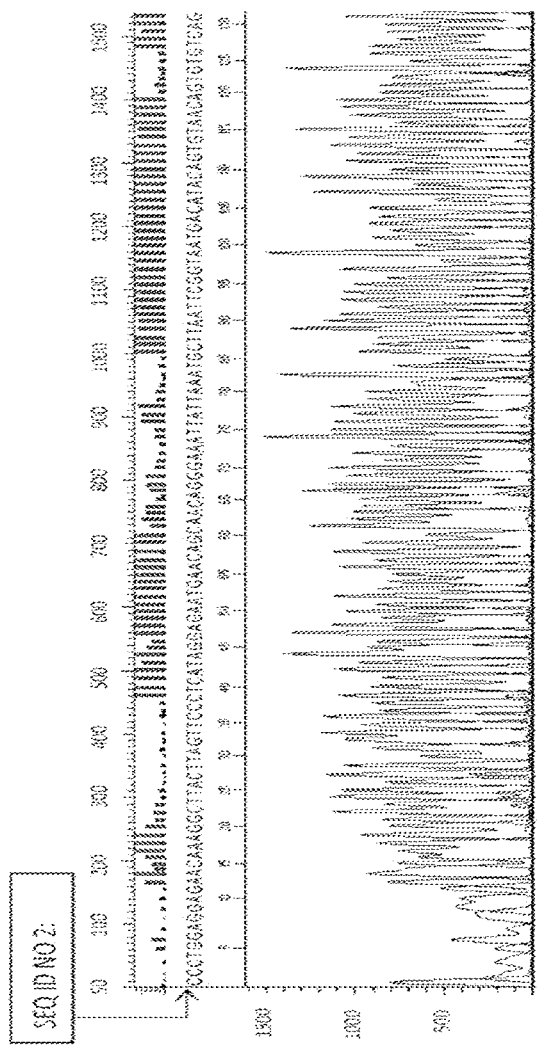
FIG. 2 illustrates sequencing data from sequence purified using Dynabeads® in 96 well plate.

FIG. 2 illustrates sequencing data from sequence purified using Dynabeads® in 96 well plate.

BigDye XTerminator® example of SEIE purification. BigDye XTerminator® (BDX) (product of Life Technologies) is used for sequencing purification in 96 or 384 well-based plates. BDX beads capture the left over waste products from the BDX reactions. The BDX beads are two bead types. The first is an ion exchange bead designed to capture negative charged items. These beads are also coated with a surface that will prevent large negative charged sample fragments from binding. The second bead-type is an ion exchange bead that captures positive charged moieties.

Figure 3:
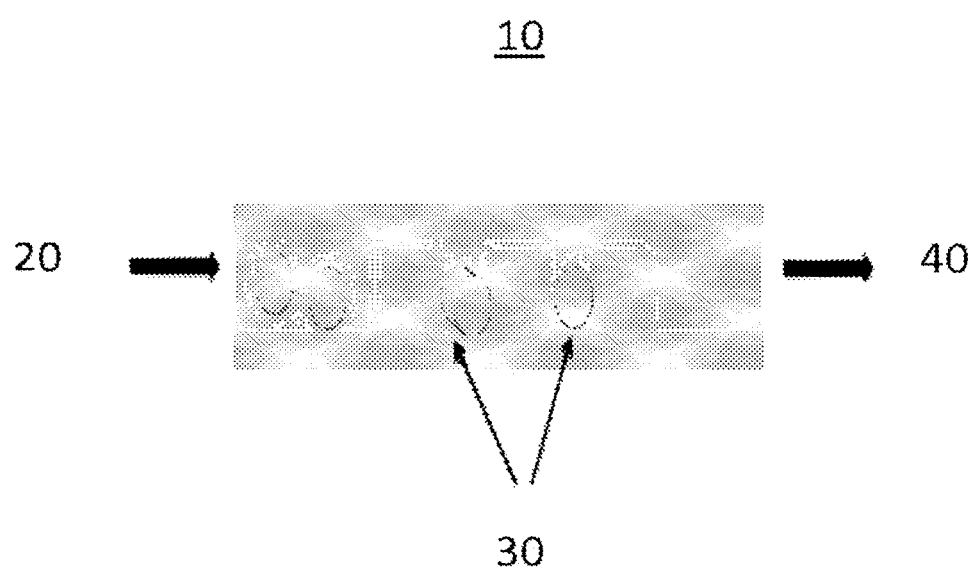
FIG. 3 illustrates a side view of a flow-channel according to one embodiment of the invention.

Procedure to Purify Sequencing Product on Chip Using BDX
1. Add 45 µl of SAM solution and 5 µl of beads solution to 10 µl of sample at RT
2. Mix the liquid (by moving back and forth or as appropriate) for 20 min
3. The supernatant containing the sequencing reaction can be separated from beads using various methods:
   a. Magnetization can be used if BDX beads are coated on magnetic core
   b. Micro pore filters can be used to retain the beads.
   c. A flow-channel 10 can be designed to retain beads when liquid passes through it, as illustrated in FIG. 3. Inlet 20 accepts a mix of beads and liquid with trapped beads 30 allowing clear liquid 40 to pass through the channel.
      a. The beads can be staged such that the first beads capture the positive charged moieties and the second stage captures the negative charged moieties. The BDX beads also have a size exclusion coating that prevents the longer DNA sample fragments from being captured. The beads can be staged so that the sample does not become clogged. This may require multiple stages of beads.
      d. Mixing can be used to promote efficient waste capture in the beads. Magnetic beads can aid mixing. The beads can transit between multiple chambers or regions in single chamber with magnets that oscillate between positions.
      e. If beads are captured in a frit then the sample can oscillate back and forth in the beads. Alternatively, a fluid path could be created where the sample is circulated through bead region. After a given number of passes, a valve is opened and the clean sample is allowed to pass to the next stage.
      f. The beads and sample can be heated to increase the reaction rate of the waste to the beads. Heating can also help when charge switch or silane beads are used.
      g. Membranes with the same ion exchange and size exclusion properties can replace the BDX beads. One membrane would capture negative ions and a second the positive ions. Mixing would be achieved as for beads in a frit.
4. Collect the liquid for sequencing readout.

The preceding descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

What is claimed is:

1. A method comprising:
   performing a single-stranded DNA sequencing assay to yield a product mixture;
   introducing the product mixture to an inlet of a flow channel in a microfluidic chip;
   flowing the product mixture through a first section along a length of the flow channel and into contact with a first microstructure in the first section, the first microstructure coated with a first reagent comprising an anion-exchange reagent configured to capture negatively-charged single-stranded DNA fragments from the product mixture, and the first microstructure coated with a second reagent comprising a size-exclusion reagent configured to prevent single-stranded DNA fragments larger than a preselected size from being captured from the product mixture;
   capturing negatively-charged single-stranded DNA fragments from the product mixture via the first microstructure to yield a first filtrate;
   after the capturing of the negatively-charged single-stranded DNA fragments, flowing the first filtrate through a second section along the length of the flow channel and into contact with a second microstructure in the second section, the second microstructure coated with a third reagent comprising a cation-exchange reagent configured to capture positively-charged single-stranded DNA fragments; and
   capturing positively-charged single-stranded DNA fragments from the first filtrate via the second microstructure to yield a second filtrate.

2. The method of claim 1, wherein the first and second microstructures comprise one or more of a microbead, a tube, a membrane, and a plate.

3. The method of claim 1, wherein the first microstructure, the second microstructure, or both are nonmagnetic, magnetic, or paramagnetic.

4. The method of claim 1, wherein one or both capturing steps comprise capturing one or more sequencing contaminants, the one or more sequencing contaminants comprising one or more of a salt, a free salt, a salt ion, an ion, a sequencing amplification compound, a short primer, a dNTP, an enzyme, a short-failed polymerase chain reaction/capillary electrophoresis product, a salt from a polymerase chain reaction/capillary electrophoresis product, and an unincorporated dideoxyNTP.

5. The method of claim 1, further comprising applying a magnetic field to the flow channel, wherein the first microstructure, the second microstructure, or both are magnetic, and are moveable in response to the application of the magnetic field.

6. The method of claim 1, further comprising controlling flow between the first and second sections using a valve, wherein the flow channel comprises a valve separating the first and second sections.

7. The method of claim 1, wherein one or more of the first reagent, the second reagent, and the third reagent comprises a silane.

8. The method of claim 1, further comprising collecting the second filtrate.

9. The method of claim 1, wherein the product mixture comprises a liquid composition, the liquid composition comprising water and compounds in solution, or in suspension, or both.

10. A method comprising:
   performing a single-stranded DNA sequencing assay to yield a product mixture;
   introducing the product mixture to an inlet of a flow channel in a microfluidic chip, the flow channel comprising a high-surface area, convoluted material located along a length of the flow channel, the high-surface area, convoluted material having a first section and a second section at different locations along the length of the flow channel, wherein the first section is coated with an anion-exchange reagent configured to capture negatively-charged single stranded and with a size-exclusion reagent configured to prevent single-stranded DNA fragments larger than a preselected size from being captured, and wherein the second section is coated with a cation exchange reagent configured to capture positively-charged single-stranded DNA fragments;

flowing the product mixture into contact with the first section of the high-surface area, convoluted material;

capturing negatively-charged single-stranded DNA fragments from the product mixture at the first section to yield a first filtrate;

after the capturing of the negatively-charged single-stranded DNA fragments, flowing the first filtrate into contact with the second section of the high-surface area, convoluted material; and capturing positively-charged single-stranded DNA fragments from the first filtrate at the second section to yield a second filtrate.

11. The method of claim 10, wherein the high-surface area, convoluted material comprises a frit, a wool, or both.

12. The method of claim 10, wherein one or both capturing steps comprise capturing one or more sequencing contaminants, the one or more sequencing contaminants comprising one or more of a salt, a free salt, a salt ion, an ion, a sequencing amplification compound, a short primer, a dNTP, an enzyme, a short-failed polymerase chain reaction/capillary electrophoresis product, a salt from a polymerase chain reaction/capillary electrophoresis product, and an unincorporated dideoxyNTP.

13. The method of claim 10, wherein one or more of the reagents comprise a silane.

14. The method of claim 10, wherein the high-surface area, convoluted material comprises a frit.

15. The method of claim 10, wherein the product mixture comprises a liquid composition, the liquid composition comprising water and compounds in solution, or in suspension, or both.

* * * * *